(12) United States Patent
Halanski et al.

(10) Patent No.: US 7,837,637 B2
(45) Date of Patent: Nov. 23, 2010

(54) SAFETY CAST

(75) Inventors: Matthew A. Halanski, Warren, MI (US); Eric Heiberg, Long Valley, NJ (US); Steven McCormick, East Stroudsburg, PA (US); Kenneth Noonan, Madison, WI (US)

(73) Assignee: EBI, LLC, Parsippany, NJ (US)

( * ) Notice: Subject to any disclaimer, the term of this patent is extended or adjusted under 35 U.S.C. 154(b) by 308 days.

(21) Appl. No.: 11/787,446

(22) Filed: Apr. 16, 2007

(65) Prior Publication Data

US 2007/0255189 A1 Nov. 1, 2007

Related U.S. Application Data

(60) Provisional application No. 60/792,380, filed on Apr. 14, 2006, provisional application No. 60/797,287, filed on May 3, 2006.

(51) Int. Cl.
*A61F 5/00* (2006.01)

(52) U.S. Cl. .................. 602/8; 602/5; 602/6; 602/7

(58) Field of Classification Search .................. 602/5–8
See application file for complete search history.

(56) References Cited

U.S. PATENT DOCUMENTS

| | | |
|---|---|---|
| 3,332,416 A | 7/1967 | Brickman et al. |
| 3,630,194 A | 12/1971 | Boardman |
| 3,908,644 A | 9/1975 | Neinart et al. |
| 3,932,526 A | 1/1976 | Koshar |
| 4,028,118 A | 6/1977 | Nakasuji et al. |
| 4,273,115 A | 6/1981 | Holland et al. |
| 4,411,262 A | 10/1983 | von Bonin et al. |
| 4,667,661 A | 5/1987 | Scholz et al. |
| 4,957,949 A | 9/1990 | Kamada et al. |
| 5,052,380 A | 10/1991 | Polta |
| 5,061,555 A | 10/1991 | Edenbaum et al. |
| 5,085,607 A | 2/1992 | Shibahashi et al. |
| 5,088,484 A | 2/1992 | Freeman et al. |
| 5,202,677 A | 4/1993 | Parker et al. |
| 5,294,375 A | 3/1994 | Kampe et al. |
| 5,342,291 A * | 8/1994 | Scholz et al. .................. 602/41 |
| 5,375,271 A | 12/1994 | Frankel |
| 5,480,708 A | 1/1996 | Cheng |
| 5,810,749 A * | 9/1998 | Maas ............................ 602/6 |
| 5,823,978 A | 10/1998 | Cueman et al. |
| 5,976,610 A | 11/1999 | Scholz et al. |
| 5,984,884 A | 11/1999 | Alvarez et al. |
| 6,139,779 A | 10/2000 | Small et al. |
| 6,328,910 B1 | 12/2001 | Askill et al. |
| 6,604,854 B1 | 8/2003 | Limburg et al. |
| 6,660,345 B2 | 12/2003 | Coates et al. |
| 6,673,030 B1 * | 1/2004 | Peel ............................... 602/6 |
| 6,673,727 B2 | 1/2004 | Morris et al. |
| 2002/0193718 A1 * | 12/2002 | Henderson et al. ............. 602/8 |
| 2003/0038397 A1 * | 2/2003 | MacAllister et al. ........ 264/222 |
| 2003/0192872 A1 | 10/2003 | Lerner |
| 2004/0112887 A1 | 6/2004 | Lerner |
| 2004/0229754 A1 | 11/2004 | Fujita |
| 2005/0104043 A1 | 5/2005 | Lucht et al. |
| 2006/0081639 A1 | 4/2006 | Lazaroff et al. |

FOREIGN PATENT DOCUMENTS

| | | |
|---|---|---|
| EP | 0276118 | 7/1988 |
| EP | 0279612 | 8/1988 |
| WO | WO2006131196 | 12/2006 |

OTHER PUBLICATIONS

Hoebel, Stacey et al. "Artificial Limb for the Study of Cast Burns". pp. 1-21, Dec. 8, 2004. (Available at The University of Wisconsin-Madison's website at http://homepages.cae.wisc.edu/~bme402/burning_limb/reports/Final_Paper.pdf).

Goto, Motonori et al. "Experimental Study on Thermal Burns Caused by Plaster Bandage" J. Jpn. Orthop. Ass. 60: 671-680. 1986.

* cited by examiner

*Primary Examiner*—Kim M Lewis
(74) *Attorney, Agent, or Firm*—Harness, Dickey

(57) ABSTRACT

Safety cast compositions for the prevention of thermal injury are provided basically comprising a curable casting material, a flexible substrate coated or impregnated with the casting material and a thermochromic material. Methods for using the safety cast to prevent cast burns in patients in need of immobilizing a body member are also provided.

24 Claims, No Drawings

SAFETY CAST

CROSS-REFERENCE TO RELATED APPLICATIONS

This application claims the benefit of U.S. Provisional Application No. 60/792,380, filed on Apr. 14, 2006 and 60/797,287 filed May 3, 2006. The disclosures of the above applications are incorporated herein by reference.

BACKGROUND

The present disclosure relates to orthopedic casting materials.

Casting is the process of forming a rigid dressing around a body member of a human or animal subject, which typically involves wetting a plaster or synthetic resin cast bandage, and wrapping the bandage around the body member. The water or other curing solvent causes a reaction that begins a curing process that may produce significant heat. Cast burns, commonly associated with plaster cast bandages, can be caused by dipping the bandage into water that is too hot, by plaster impregnated casting bandages having rapid setting times, or by wrapping too many layers of casting tape around a body member. Some of the problems of cast burns are skin surface burns, compartment syndrome, pressure sores, cast saw burns, and nerve injuries.

In regard to skin surface burns, time and temperature are considered as two important variables for development of skin burns. In some cases, temperatures of 50-60 degrees Celsius for 60-100 seconds can result in third degree burns. Temperatures of about 43 degrees Celsius for prolonged time can result in skin damage.

There is, therefore, a need for casting materials that help reduce the likelihood of burns.

SUMMARY

In various aspects, a casting material composition for preventing cast burns is provided. In one aspect, the casting material comprises a flexible substrate coated or impregnated with a curable casting matrix and a thermochromic material.

In certain aspects, a casting material composition for preventing cast burns comprises thermochromic materials that can be reversible, irreversible and change from one color to a second color or from one color to transparent upon reaching a predetermined temperature. The casting material can comprise natural and synthetic casting systems including Plaster or Paris and isocyanate-functional prepolymer curable matrices having a thermochromic material present at about 0.1% to about 10% by weight of the composition. Thermochromic materials may comprise thermochromic dyes and pigments comprising electron donating/accepting organic chromagens, thermochromic liquid crystals and thermochromic leuco dyes that can change color from one color state to another color state between 20° C. and 60° C.

The present technology also provides methods for determining whether the temperature of the cast is below a predetermined temperature and for enhancing safe usage of the casting material to prevent cast burns on a subject. Methods comprise applying an orthopedic cast material composition to the body member after wetting the curable casting matrix. The cast composition comprises a curable casting matrix, a flexible substrate coated or impregnated with the curable casting matrix and a thermochromic material. The casting practitioner can then visually monitor the cast as the cast is curing to determine whether the cast has reached a predetermined temperature that is capable of causing a cast burn. If the cast material does not change color at the predetermined temperature, then the cast can be allowed to harden on the immobilized body member.

Applicants have found that methods and casting materials of this technology provide benefits versus casting materials among those known and practiced in the art. Such benefits can include enhanced ability to determine the skin burning potential of a newly applied cast, prevention of skin cast burns and the ease and lower cost of training casting practitioners to recognize casts that can potentially burn the skin of their patients and to recognize casts that are causing thermal damage to the skin during the casting procedure. Further areas of applicability of the present technology will become apparent from the detailed description provided hereinafter.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings (such as "Curable Matrices") used herein are intended only for general organization of topics within the disclosure of this technology, and are not intended to limit the disclosure of the technology or any aspect thereof. In particular, subject matter disclosed in the "Introduction" may include novel technology, and may not constitute a recitation of prior art. Subject matter disclosed in the "Summary" is not an exhaustive or complete disclosure of the entire scope of the technology or any embodiments thereof.

The citation of references herein and during prosecution of patent applications regarding this technology does not constitute an admission that those references are prior art or have any relevance to the patentability of the technology disclosed herein. All references cited in the Description section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific Examples are provided for illustrative purposes of how to make, use and practice the compositions and methods of this technology and, unless explicitly stated otherwise, are not intended to be a representation that given embodiments of this technology have, or have not, been made or tested.

As used herein, the words "preferred" and "preferably" refer to embodiments that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that a recitation that an embodiment can or may comprise certain elements or features does not exclude other embodiments of the present technology that do not contain these elements or features.

The present disclosure provides orthopedic casting materials that can provide a visual indication or other warning of potentially harmful temperatures. As referred to herein, an "orthopedic safety cast" is a device that encloses, in whole or in part, a body member (e.g., a forearm or leg) of a human or animal subject. Such casts can be used for the prevention of injury, or in the treatment and management of conditions such as bone fractures. The present technology provides orthopedic casting materials comprising a flexible substrate coated or impregnated with a curable casting matrix and a thermochromic material.

Specific compounds, compositions and other components used in the orthopedic safety casts are pharmaceutically and cosmetically acceptable. As used herein, such a "pharmaceutically and cosmetically acceptable" composition or component for use in human or animal subjects, is one in which there are no undue side-effects including toxicity, irritation, and allergic response, commensurate with a reasonable benefit/risk ratio assessed in sound medical judgment.

Curable Matrices

The safety cast compositions of the present technology comprise curable matrices, which can comprise any natural or synthetic casting material that can be hardened upon contact with a solvent. In some embodiments the safety casts comprise a moisture curable matrix that is curable upon contact with moisture, such as to water, water vapor (e.g., through exposure to air), or through any other means sufficient to provide the moisture curable matrix with water so as to initiate curing. In some embodiments, the curable matrices can be cured with non-aqueous solvents.

Curable matrices of the present disclosure comprise and can be prepared using non-synthetic hardenable compounds commonly used in the art of casting tapes and bandages. Such hardenable matrices can include cementation casting materials including alpha and beta calcium sulfate hemihydrate cements (Plaster of Paris), gypsum based cements, and the like, and mixtures thereof. Calcium sulfate hemihydrate containing casting matrices can be of the types which are described in U.S. Pat. No. 3,332,416, Brickman et al., issued Jul. 25, 1967.

Other curable matrices include synthetic resin casting matrices, such as water-activated or water-curable synthetic resin compositions, and thermoplastic resin compositions. Useful thermoplastic resin compositions include Varaform, such as are described in U.S. Pat. No. 4,273,115, Holland et al., issued Jun. 16, 1981 (composite materials of a fiber mesh and a thermoplastic resin, such as a polyester, e.g., polycaprolactam resin; Varaform previously known as hexcelites are available commercially from Douglass and Sturgess, Inc., San Francisco, Calif.).

In some embodiments, the moisture curable casting matrix includes classes of casting resins known as the polyurethanes. Polyurethane casting matrices can comprise a water-curable mixture of an isocyanate and a hydroxy-containing compound. Such synthetic moisture curable matrices of the present disclosure can comprise, and can be prepared by reacting, one or more polyisocyanates and one or more polyols. The polyisocyanate can be aliphatic, cycloaliphatic, or aromatic diisocyanates, triisocyanates, or tetraisocyanates, as well as biurets, isocyanurates, and similar oligomers of these. Examples of useful polyisocyanates can include, without limitation, toluene diisocyanates (TDI), including the 2,4 and 2,6 isomers and mixtures of these isomers; diphenylmethane diisocyanates (MDI), including the 4,4', 2,4', and 2,2' isomers and mixtures of these isomers; hydrogenated diphenylmethane diisocyanates, aromatic polyisocyanates derived from phosgenation of the condensation product of aniline and formaldehyde (polymeric MDI), hexamethylene diisocyanate, isophorone diisocyanate, octamethylene diisocyanate, trimethylhexane diisocyanates, dodecamethylene diisocyanates, cyclopentane diisocyanate, cyclohexane diisocyanate, tetramethylxylene diisocyanate, and biurets, allophonates, isocyanurates, and substituted derivatives of these, such as carbodiimide-containing polyisocyanates. In some embodiments, isocyanates include polymeric diphenylmethane diisocyanates (polymeric MDI's).

The polyisocyanate can be reacted with at least one polyol. Examples of suitable polyols can include, without limitation, polyether polyols, polyester polyols including polycaprolactone polyols, and monomeric diols and triols such as 1,6-hexanediol. Preferred polyols include polyethylene oxide and polypropylene oxide diols and triols, having a molecular weight of at least about 2,000, preferably from about 2,000 to about 4,000, more preferably from about 3,000 to about 4,000. Preferably the polyol has a hydroxyl number of from about 28 to about 56, preferably from about 28 to about 46, more preferably from about 35 to about 40. As referred to herein, the "hydroxyl number" is the number of milligrams, per gram of polyol, of potassium hydroxide having an acid neutralization capacity equal to the polyol. Examples of polyols can include PPG 3025, having a molecular weight of about 3,000 and a hydroxyl number of from about 35 to about 40, sold by Lyondell Chemical Company, and QO Polymeg 3000, having a molecular weight of from about 2,800 to about 3,000 and a hydroxyl number of from about 37 to about 40, sold by Great Lakes Chemical Corporation.

The synthetic curable matrices of the present disclosure are not limited to polyurethanes/polyisocyanate prepolymer matrices. The curable matrices can include any other curable resin that will satisfy the pharmaceutical and aesthetic requirements of a medical and/or orthopedic cast. A number of classes of water-curable resins known in the art are suitable, including cyanoacrylate esters, and, when combined with moisture sensitive catalysts, epoxy resins and prepolymers terminated at their ends with trialkoxy- or trihalo-silane groups. For example, U.S. Pat. No. 3,932,526, Koshar, issued Jan. 13, 1976, describes that 1,1-bis(perfluoromethylsulfonyl)-2-aryl ethylenes cause epoxy resins containing traces of moisture to become polymerized.

In various embodiments non-aqueous based curing matrices used as orthopedic casting materials are known and useful. Resin systems other that those which are water-curable can be used in the present disclosure, although the use of water based curing matrices for orthopedic casting tapes are generally regarded by practitioners as preferred, due to their convenience, safety and familiarity. In some embodiments of the present disclosure, curable matrices that are not cured in water can include those disclosed in U.S. Pat. No. 3,908,644, Neinart et al., issued Sep. 30, 1975, in which a bandage is impregnated with difunctional acrylates or methacrylates, such as the bis-methacrylate ester derived from the condensation of glycidyl methacrylate and bisphenol A (4,4'-isopropylidenediphenol) are contemplated. The curable matrix can be hardened upon wetting with solutions of a tertiary amine and an organic peroxide. For example, U.S. Pat. No. 3,630, 194, Boardman, issued Dec. 28, 1971, describes an orthopedic tape impregnated with acrylamide monomers whose polymerization is initiated by dipping the bandage in an aqueous solution of oxidizing and reducing agents (known in the art as a redox initiator system).

In some embodiments, the synthetic resins can further include a catalyst. The reactive curable synthetic matrix once exposed to water can be controlled with a suitable catalyst. In some embodiments, the catalyst further enables the cross-linking reaction between the polyurethane prepolymer and water. However, proper selection of the catalyst and the degree of crosslinking is to be controlled such that the reactivity of the reaction does not allow the cast to become rigid before the application and shaping of the safety cast is complete. Examples of suitable catalysts for use in polyisocyanate prepolymer casting matrices can include tertiary amines; organometallic compounds; tertiary amine catalysts such as tertiary alkanolamines, for example, dimethylethanolamine and dimethylaminodiethyl ether; 2,2'-dimorpholinodialkylethers such as 2,2'-dimorpholinodiethylether (DMDEE), available commercially from Texaco, Inc., as Thancat DMDEE; and 2,2'-dimorpholinyldialkylethers, such as 4-[2-[methyl-2-(4-morpholinyl)ethoxy]-ethyl]morpholine (MEMPE). The catalyst is preferably included in amounts of from about 0.1% to about 10% by weight of the composition.

In addition to the synthetic and natural hardenable curing matrices, the orthopedic safety cast composition of the present disclosure can further include fillers, binders, antioxidants, viscosity modifiers, and UV stabilizers. Suitable fillers can include inorganic or organic, particulate or fibrous composites which are insoluble in the curable matrix. Fillers/binders can include spheres, bubbles, expandable bubbles, particulate materials, filaments, microfibers, flakes, as well as combinations of these. In some embodiments, the binder can be mixed with the thermochromic material for example, when the thermochromic material is an aqueous slurry comprising one or more thermochromic dyes or pigments, thermochromic liquid crystals or thermochromic electron donating/accepting chromagen systems described herein. In some embodiments, the binder can be a composition comprising vinylacetate/vinylester/ethylene polymers and the like.

In some embodiments, the fillers can have a solid, porous, or hollow structure. In some embodiments, fillers useful in the present disclosure can be light-weight and irregularly shaped, thereby preferably ensuring sufficient void volume to render the composite sufficiently porous to facilitate the transfer of moisture vapor from the patient.

Thermochromic Materials

The thermochromic materials of the present disclosure can be intermixed with casting materials including the curable matrices and/or directly onto flexible substrates in which it is desirable to provide a color change when the curing casting materials have released sufficient heat to pose a burn risk to the patient. As used herein, the term "thermochromic material" or "thermochromic dye or pigment" generally refers to substances having the ability to respond to changes in temperature by altering its ability to absorb, transmit or reflect light. Thus, the terms "thermochromic" and thermochromic-based changes in "color," as used herein, can refer to any change in a visualizable indication in the casting material in which the thermochromic material is present. Such visualizable indications include changes in visible color proper, in fluorescence, in luminescence, phosphorescence, and like phenomena, which indications can be development of the color or other visualizable phenomenon, elimination of the color or other visualizable phenomenon, or change from one to another color or other visualizable phenomenon. The change is one that is visualizable, i.e., any change that is apparent when the casting material is viewed by the human eye, either through or without a filter, and either with or without photostimulation, such as illumination by ambient light or exposure to light of a specific wavelength. The thermochromic material can be dispersed throughout the casting material, can be localized in or on the flexible substrate, can be localized in discrete zone(s) that extend throughout the thickness of the cast, or can be localized, e.g., in a surface layer of the cast. When localized, the zone(s) in which the thermochromic material is located, can be shaped or arranged in a desired geometric pattern or patterns, including but not limited to the shapes of written characters.

In the field of orthopedic casting, the casting material is applied immediately after wetting and can be shaped and molded until the cast has retained its final shape which can take up to 90 minutes. In many instances it is clearly desirable to know when casting materials are curing at a rate that is accompanied by production of excessive heat. In this regard, it is desirable to view a cast while it is being applied and once applied, for the duration of the set-up period, and to note whether at least a portion of the cast has reached a temperature that can cause a first, second or third degree burn to the skin of the patient.

Thermochromic materials come in a variety of colors and chemistries. Broadly speaking, there are three classes of thermochromic materials, these include thermochromic electron donating/electron accepting organic chromagens, thermochromic liquid crystal compositions, and thermochromic leuco dyes. The thermochromic materials of the present disclosure are not limited to any one class of thermochromic materials described above. Furthermore, the thermochromic material can be dispersed in an aqueous solvent or a non-aqueous solvent when applied to the casting materials described herein. Factors that can be considered when selecting thermochromic materials for the present disclosure can include their color transition temperature, their chemical and physical compatibility with the other casting components, primarily, the curable matrix and flexible substrate and their degree of toxicity to the human or animal subject. In various embodiments, the thermochromic material can be included into the curable casting matrix, surface coated onto the cast or painted or applied onto the flexible substrate (e.g. natural or synthetic fabrics, yarns and fibers, e.g. fiberglass). In some embodiments, the thermochromic material can be from about 0 to about 15%, or from about 0 to about 10% or from about 0.001 to about 10% or from about 0.01 to about 10% by weight of the curable casting matrix. In some embodiments, the thermochromic material can be from about 0 to about 15%, or from about 0 to about 10% or from about 0.001 to about 10% or from about 0.01 to about 10% by weight of the casting material.

In some embodiments of the present disclosure, the thermochromic material comprises thermochromic electron donor organic chromagens mixed with electron accepting compounds and various other components including without limitation, aliphatic alcohols and/or aliphatic alcohol esters. In various embodiments, the electron donative coloring organic compounds can include without limitation, diphenylmethane phthalides, phenylindolyl phthalides, bridged phthalides, indolyl phthalides, diphenylmethane azaphthalides, phenylindolyl azaphthalides, fluorans, styrylquinolines, polythiophenes and diazarhodamine lactones. In various embodiments, the thermochromic electron donative organic chromagens described above further comprise electron accepting compounds which are characterized as acid containing or acid like compounds that cause color development of the electron donative coloring organic compounds. These electron accepting compounds can include monophenols to polyphenols; their derivatives which have substituent groups such as one or more of the, preferably C1-C18, aliphatic groups, aryl groups, acyl groups, alkoxycarbonyl groups, carboxy groups, carboxyesters, amido groups, and halogen groups; and phenol-aldehyde condensed resins such as of bis type and tris type phenols. They can be metal salts of the aforementioned compounds having phenolic hydroxyl groups. These electron donative/accepting coloring organic compounds exhibiting thermochomism are of the types which are described in U.S. Pat. No. 4,028,118, Nakasuji et al., issued Jun. 7, 1977; U.S. Pat. No. 4,957,949, Kamada et al., issued Sep. 18, 1990; U.S. Pat. No. 5,294,375, Kampe et al., issued Mar. 15, 1994; and U.S. Pat. Application Pub. No. 2004/0229754, Fujita, published Nov. 18, 2004 and U.S. Pat. Application Pub. No. 2005/0104043, Lucht et al., published May 19, 2005. In some embodiments, the thermochromic materials having one or more electron donative/accepting coloring organic compounds further comprise binders, fillers, anti-oxidants, emulsifyers, dispersion agents, carriers and the like. Thermochromic electron donative/accepting coloring organic compounds include carriers including polyurethanes, polysoloxanes, polydienes, polyacrylates, poly (ethylene terepthalates), polyvinyl alcohols, polyamides, polyvinyethers, polyacrylamides polyvalent isocyanate functional prepolymers, polyester resins, epoxy resins, plant oils, cellulose and hydrocarbon resins.

In various embodiments, the electron donative/accepting coloring organic compounds can have a metachromatic reversible color change from color to color, from color to a colorless transparency at various temperatures. In some embodiments, the thermochromatic electron donative/accepting coloring organic compounds described herein can further be microencapsulated by any conventional microencapsulation technique, for example, as described in U.S. Pat. No. 4,028,118, Nakasuji et al., issued Jun. 7, 1977 (Examples 30-40). As such, the thermochromic electron donative/accepting coloring organic compounds can be microencapsulated for use in orthopedic casting compositions. The electron donative/accepting coloring organic compounds can be added to specific vehicle formulations that are made compatible with naturally occurring plaster and gypsum cement curable matrices and synthetic curable matrices described above.

Other thermochromic materials can include thermochromic liquid crystal materials that have the ability to reversibly change from a colorless transparent color at or above a predetermined temperature range and changes to a specific color when it reaches the predetermined temperature. Thermochromic liquid crystals include those that are well known in the art, such as those popularized as color changing components of mood rings and self-adhesive thermometers. One well known class of thermochromic liquid crystals includes the thermochromic cholesteric liquid crystals (CLCs). Thermochromic CLCs exhibit a helically twisted molecular structure wherein the pitch p of the molecular helix is related to the reflected wavelength .lambda. and the average refractive index n of the liquid crystal by equation (1)

$$\lambda = n.p \quad (1)$$

In thermochromic CLCs, the reflection wavelength $\lambda$ shows a significant temperature dependence. If the reflected wavelength is inside the visible range, the thermochromic CLC material undergoes a visible color change upon variation of the temperature. As the CLCs are optically birefringent, they typically do not reflect a single wavelength, but a narrow band of wavelengths wherein the bandwidth $\Delta\lambda$ is defined according to equation (2)

$$\Delta\lambda = \Delta n.p \quad (2)$$

with $\Delta n$ being the birefringence of the liquid crystal material. The thermochromic effect described above can be manipulated to produce a wide array of thermochromic dyes and pigments for use in temperature sensing materials as contemplated in the present disclosure including orthopedic casting materials.

For the above mentioned applications, typically thermochromic CLC compositions can be used comprising achiral and chiral liquid crystalline or mesogenic compounds, which can be encapsulated as small droplets in light transmissive polymer microcapsules, for example, of gelatine or gum arabic, or in a continuous matrix of transparent binder polymers. In some embodiments, the thermochromic CLC composition can exhibit a cholesteric phase and an underlying smectic phase, i.e., a smectic phase below the temperature range of the cholesteric phase. Thermochromic material compositions comprising CLCs are described for example, in U.S. Pat. No. 6,660,345, Coates et al., issued Dec. 9, 2003 and U.S. Pat. No. 6,328,910, Askill et al., issued Dec. 11, 2001. In some embodiments, thermochromic CLCs and chiral dopants that can be used in the manufacture of thermochromic liquid crystal materials can include: cholesteryl-, dicholesteryl-, cholestanyl-, sitosteryl-, and cyanobiphenyl-organic esters, -halides, and -alkyl carbonates. In some embodiments, the cholesteric liquid crystals described above can be microencapsulated in light transmissive polymeric materials and can be formulated into dyes, pigments, inks and paints for use in synthetic polymer plastics and the like. The thermochromic material comprising thermochromic CLCs can display a spectrum of colors ranging from reflection color of red (600 nm) at 27° C. through yellow and green to light blue (480 nm) at 65° C. In some embodiments, the casting materials can include a plurality of thermochromic liquid crystals with different color change temperatures, capable of displaying different colors at different predetermined temperatures.

Thermochromic materials can comprise reversible thermochromic CLCs which are transparent except when the CLCs are heated to a predetermined temperature at which time the transparency will shift to a visible color. Such encapsulated CLCs, including those that have color change temperature ranges between 35° C. to 40° C. and 40° C. to 45° C., are commercially available from Cole-Parmer Instrument Co. Vernon Hills, Ill. and from Hallcrest of Glenview, Ill. Microencapsulations of thermochromic materials having predetermined temperatures ranging from 0° C. to 100° C. are also commercially available from American Thermal Instruments, Inc., Beavercreek, Ohio and from Color Change Corporation, Streamwood, Ill.

In various embodiments, thermochromic materials of the present technology can comprise a class of thermochromic dyes and pigments also known in the art as leuco dyes. A leuco dye is a dye whose molecules can acquire two forms, one of which is colorless. For example, the spiro form of an oxazine is a colorless leuco dye; the conjugated system of the oxazine and another aromatic part of the molecule is separated by a $sp^3$-hybridized "spiro" carbon. After protonating a part of the molecule, irradiation with UV light, or introducing another change in electromagnetic irradiation, the bond between the spiro carbon and the oxazine interrupts, the ring opens, the spiro carbon achieves $sp^2$ hybridization and becomes planar, the aromatic group rotates, aligns its π-orbitals with the rest of the molecule, and a conjugated system forms, with ability to absorb photons of visible light, and, therefore, appear in one colored state. At various temperatures, leuco dyes can change from one color state to another color state at a predetermined temperature. Each species of thermochromic dye or pigment has an inherent temperature that predetermines at what temperature that dye or pigment will change color. In various embodiments, the thermochromic material comprising thermochromic leuco dyes will change from a colored dye at one temperature to a different color (or transparent) form at a predetermined temperature. In some embodiments, the thermochromic material comprising leuco dyes or pigments will change from one color to another color.

Thermochromic materials comprising leuco dyes can be mixed with the curing matrix or coated onto the flexible substrate in the form of inks and aqueous based slurries. As used herein, thermochromic materials comprising leuco dyes can include thermochromic leuco dyes, thermochromic leuco pigments, thermochromic leuco inks and mixtures thereof. In some embodiments, the thermochromic leuco dye comprises a dried powder. In some embodiments, the thermochromic leuco dye or pigments can be encapsulated in a microcapsule, additionally containing organic solvents, acids and salts. In some embodiments, the thermochromic materials can contain thermochromic dyes and thermochromic pigments and mixtures thereof. In various embodiments, the thermochromic leuco dyes (including thermochromic leuco dye dispersions) and leuco dye systems can be formulated by encapsulating the thermochromic dye or pigment together with a weak acid, a dissociable salt and a solvent. The solvent can remain solid until the predetermined temperature is reached. The solvent can be selected to have an average melting point (m.p.) that is at a predetermined temperature, e.g. a temperature at or just below (e.g. 0-3° C. below) the temperature at which a patient's tissue (skin or other tissue structure) would begin to suffer thermal damage. In some embodiments, the solvent used in the preparation of encapsulated leuco dyes and pigments can include aliphatic hydrocarbons, fatty alcohols and the like and mixtures thereof. In some embodiments, the solvent comprises a mixture of alcohols having an average melting point temperature that is a predetermined temperature such as 43° C., 44° C., 45° C., 46° C., 47° C. or 48° C., such as for example, myristyl alcohol (m.p. 37-40° C.) and palmityl alcohol (m.p. 47-50° C.).

The aqueous slurry of thermochromic leuco dyes and pigments can be formulated so as to provide a variety of color changes. Preferably, the thermochromic aqueous slurry provides a reversible color change from colored to colorless which occurs at a temperature range of between about 35° C. and 50° C. Depending on the dyes included in the thermochromic slurry, the color change can be from a first color to a second color. For example, by adding a non-thermochromic yellow dye with a thermochromic red slurry, the color appears orange at ambient temperature, then changes to yellow at elevated temperatures. In various embodiments, mixing a blue thermochromic slurry with a non-thermochromic yellow dye, a color change will occur from green to yellow. Accordingly, mixing blue thermochromic slurry with a non-thermochromic red dye, the color change will be from purple to red. A variety of other thermochromic aqueous slurries can be mixed with non-thermochromic dyes as described above to cause a color to color change at one or more predetermined temperatures. In various embodiments, thermochromic aqueous slurries can include blue, black, gray, pink, magenta, red, orange, green and purple and mixtures thereof. In various embodiments, the leuco dyes and pigments are encapsulated in a colorless polymeric material along with other chemicals required to produce their thermochromism. The microcapsule size can vary from one micron to 50 microns in size. Preferably, the microcapsules are 1 to 30 microns, preferably from 1 to 15 microns, more preferably from 2 to 10 microns. Leuco dyes suitable as thermochromic materials of the present disclosure are commercially available from a variety of sources including Liquid Crystal Resources, Glenview Ill., Color Change Corp., Addison, Ill. and Matsui International Inc., Tokyo JP., and Chemsong, Inc., West Chicago, Ill.

In various embodiments, the thermochromic materials described herein can be dried to a powder and resuspended in an appropriate solvent and combined with acrylic or polyolefin based resins for use in synthetic curable matrices. Other vehicles for resuspending the thermochromic materials can include polyolefins like polyethylene, polyethylene copolymers, polyethylene terpolymers, polypropylene, polypropylene copolymers, and polypropylene terpolymers. Also suitable are polyvinyl chloride and its copolymers and terpolymers, polystyrene and its copolymers and terpolymers, and other materials known to those skilled in the art. Thermochromic materials, including thermochromic leuco dyes are commercially available specifically formulated for incorporation into plastics and the like, for example, thermochromic aqueous screen inks with binders, (H.W. Sands Corp., Jupiter, Fla. USA). Thermochromic materials that are solvent compatible for example, with glycols can be admixed with polyol containing solutions including polyester polyols and polypropylene ether glycols and the like. Water soluble thermochromic aqueous slurries described above can be intermixed with conventional slurries of Plaster of Paris, Gypsum cement and the like.

When a curable matrix is formulated according to the present disclosure, the dyes and/or pigments may be mixed with a (matrix and flexible substrate) compatible binder. Such binders are readily known in the art. Binders are preferably chemically compatible with the dyes and pigments they contain and with the natural or synthetic curable matrices they are admixed with. The binder preferably does not interfere with the function of the thermochromic material nor be toxic to the patient. In some embodiments, the thermochromic and non-thermochromic dyes and pigments are readily supplied in a solvent or water compatible binder that can be intermixed with the curable matrix.

In various embodiments, the thermochromic materials described above can be formulated as screen inks that can bind to and remain permanent on fabrics, yarns and synthetic fibers. The fabric compatible thermochromic inks can then be applied to the flexible casting tape which can include without limitation woven, knit, and non-woven fabrics of natural and/or synthetic fibers, including, without limitation, fiberglass fibers.

In some embodiments, thermochromic materials for the casting composition can be mixed with non-thermochromic dye. For example, a purple casting material can be formulated by admixing a blue thermochromic material with a red non-thermochromic dye or pigment. It is to be understood that other colors and combinations of colors are inclusive of use in this disclosure. Non-thermochromic dyes and pigments include those described in U.S. Pat. No. 5,061,555, Edenbaum et al., issued Oct. 29, 1991 and U.S. Pat. No. 5,052,380, Polta, issued Oct. 1, 1991.

Casting Substrates

The compositions of this technology can also comprise a substrate onto which the prepolymer is impregnated. As referred to herein, "impregnated" is the application of the prepolymer to the substrate in a manner which allows the substrate to reach a desired degree of rigidity upon curing of the resin. Such application can be, for example, by coating of the resin on the surface of the substrate, or deposition of the resin into pores or interstitial spaces within the substrate. The tape, when impregnated with the curable resin, preferably has sufficient flexibility so that it can be molded about a limb without excessive pressure. The casting material is at least partially impregnated with a curable resin. Preferably, the resin mixture can flow into the capillary spaces between fibers of the fabric.

The substrate can be a sheet (herein "casting tape") for example, having an open-weave structure of a fibrous material. The types of fabric upon which the Plaster of Paris or curable polyisocyanate prepolymer is coated or in which such plaster or prepolymer can be impregnated have been well described in the art (e.g. U.S. Pat. No. 4,667,661, Scholz et al., issued May 26, 1987 and U.S. Pat. No. 4,411,262, von Bonin et al., issued Oct. 25, 1983). In some embodiments, the plaster or curable resin mixture that is impregnated into the tape can consist on a percent weight basis, from about 25% to about 60%, or from about 30% to about 50%, or from about 35% to about 48%, or from about 40% to about 45%, by weight of the impregnated tape.

The sheet can be semi-rigid or flexible and can be porous so that the curing agent can penetrate into the roll of fabric and contact all parts of the resin. Examples of suitable sheets are woven, non-woven or knit fabrics can include natural or synthetic fibers, including acrylic fibers, fiberglass, polyester fibers, polypropylene fibers, polyaramide fibers, polyamide fibers, carbon fibers, glass fibers, multifilament fibers, polyethylene fibers, polyacrylonitrile copolymer fibers, elastomeric fibers, non-elastomeric fibers, cotton fibers, natural fiber yarn, wool fibers, flax fibers, rayon fibers, and mixtures thereof. In some embodiments, the sheets can include knit fiberglass fabrics, although fabrics of cotton and polyester, for example, can also be used. The openings are in the preferred range of 250-280 mesh-size openings per square inch, for example, 265 openings per square inch. A typical knit fiberglass can include sheets manufactured by Johnson and Johnson, New Brunswick, N.J. The structural strength and textural characteristics with respect to porosity and thickness are chosen to provide rapid and thorough mixing of the curing agent with the impregnated resin component. In some embodiments the fabric selected is to be thin with a high surface-to-volume ratio.

The casting tape can be manufactured in lengths from about 2.7 m (3 yards) to about 4.1 m (4.5 yards), or from about 3.6 m (4 yards) to about 3.8 in (4.2 yards) in length or from about 2.5 cm (1 inch) to about 25.4 cm (10 inches), or from about 2.5 cm (1 inch) to about 12.7 cm (5 inches), wide and can be impregnated with one or more curable resin materials by an environmentally controlled process to eliminate moisture which would otherwise cause the premature hardening and/or low shelf life of the resulting impregnated fabric. The resulting plaster or resin coated fabric is formed in a roll wound up on a plastic core and then packaged within an hermetically sealed container. In some embodiments, the cylindrical core can include cores described in U.S. Pat. No. 5,984,884, Alvarez et al., issued Nov. 16, 1999. Such cylinders preferably have multiple "L"-shaped projections that extend radially outward from the core of the cylinders. When it is ready for use, the package is opened and the roll is fully immersed in water for sufficient time for the water to seep into the porous material and displace the air. The roll is then unwound during the formation and wrapping of the cast in a manner well known to the orthopedic surgeon or specialist.

Methods

In some embodiments, the safety cast compositions are formulated for the prevention of cast burns and other injuries and trauma experienced by patients having plaster or synthetic casts applied to immobilize members of their body. The present disclosure provides methods for an orthopedic practitioner to visually determine whether the casting material to be applied to the body member of a human or animal subject is likely to cause a cast burn. Furthermore, the orthopedic practitioner can readily determine whether the applied cast using the casting materials described herein, will likely cause a cast burn without the aid of thermal measuring devices such as thermometers and thermocouples employing data acquisition in real time while the cast is curing. In various embodiments, the casting materials comprise a thermochromic material that will change from one color to another transition color at a predetermined temperature. The curable casting matrix is preferably nontoxic in the sense that it does not produce toxic and harmful vapors during curing which can be harmful to either the patient or the person applying the cast and also that it does not cause substantial skin irritation either by chemical irritation or the generation of excessive heat during cure.

The present disclosure provides for methods of determining whether a water containing curing agent used to cure a moisture curable casting material is capable of causing a cast burn on a body member of a human or other animal subject when said casting material is applied to a human or other animal subject in need of said casting material comprising the steps: (a) immersing a temperature responsive orthopedic safety casting material according to claim 1 into the water containing curing agent, (b) allowing the orthopedic safety casting material to hydrate with said curing water and; (c) monitoring the temperature responsive orthopedic safety casting material visually to determine if a predetermined temperature is indicated by a color change of the temperature responsive thermochromic material dispersed in the temperature responsive orthopedic safety casting material.

A useful parameter in predicting whether a burn cast will ensue after the application of casting materials is the temperature of the water in which the moisture curable casting tape is initially immersed. In this regard, the present disclosure provides for casting materials that can immediately alert the orthopedic practitioner that the curing water is too hot and that the practitioner should not apply the casting material onto the patient.

In some embodiments, the casting material of the present disclosure comprises a curable casting matrix capable of hardening, a flexible substrate coated or impregnated with the curable casting matrix and a thermochromic material that can function to indicate a predetermined temperature when immersed in water specifically prepared for curing the moisture curable casting matrix. In some embodiments, if the water temperature is at or above 43° C. that is predetermined to be at a temperature sufficient to cause a skin burn, the safety cast material comprising a thermochromic material having a color change temperature of 43° C., or 44° C., or 45° C., or 46° C., or 47° C. or 48° C. can reversibly or irreversibly change from an opaque color to a transparent or lighter color, from one color to another color, or change from a transparent or lighter color to an opaque color.

In some embodiments, the casting material can also include one or more additional thermochromic inks with predetermined temperatures that are higher or lower than 43° C. to aid the orthopedic practitioner in deciding when to apply the wetted casting material to the human or animal subject. For example, a casting tape comprising a blue thermochromic material with a predetermined color change temperature of 40° C., a second red thermochromic material with a predetermined color change temperature of 43° C., and a yellow non-thermochromic pigment can be immersed in a water curing bath that is prepared at 41° C. At the outset, the casting tape has a brown color, but when immersed in the 41° C. water, the casting tape will reach the first predetermined temperature, and the casting tape will turn from brown to orange, an indicia that could alert the casting practitioner, that the casting tape has the potential to burn the skin if applied to the patient without any precautionary measures. After 4 minutes of curing, the cast temperature has reached a second predetermined temperature of 43° C., and the technician can readily visualize that the cast has changed color from orange to yellow thus indicating that immediate action to remove the cast from the patient is warranted. Although the above method is an example of one or more thermochromic materials present in a safety casting system, the colors used can be interchangeable depending on their predetermined temperatures and choices of non-thermochromic pigments and dyes. Such choices are routinely made by those of ordinary skill in the art of casting matrix manufacturing. The present disclosure also provides methods for determining whether an applied cast is below a predetermined temperature to ensure safe usage of the orthopedic safety cast to prevent and mitigate cast burns.

Orthopedic casts of the present technology can be used in the prevention or treatment of a variety of disorders, for example, application of the safety cast to the foot, ankle, knee, torso, back, neck, hand, or arm of a human or other animal subject. In some embodiments, safety casts of the present disclosure, can be used as casts, splints, braces, or protective devices regarding hallux spica, osteotomies, bunionectomies, diabetic foot ulcerations, fractures, segmental disorders, fusions, arthrodosis, skin grafts, tendon injuries, foot-drop, club feet, neuropathic disorders, ankle sprains, Jones fractures, shin splints, congenital hip dislocations, hip luxation, hip dislocations, rib fractures, gastric ruptures, and functional Collies' fracture treatment. Casts can be formed, for example, as minerva casts, hallux casts, cylinder casts, hinged knee casts, femoral braces, tibia braces, hip spica casts, hyperextension braces, braces for scoliosis treatment, braces for kyphosis treatment, finger splints, short arm casts, scaphoid casts, Bennett's fracture casts, long arm casts, shoulder spica, acromioclavicular and clavicular bandage, velpeau bandage, tracheotomy protection brace, glove spica casts, short arm casts, long arm casts, acromioclavicular and clavicular bandages, functional forearm braces, functional humeral braces, dynamic hand splinting, and static hand splinting. Methods of the present disclosure generally comprise the steps of: applying an orthopedic safety cast to the body member; monitoring the orthopedic safety cast over a period of time during at least part of the curing process to determine whether the orthopedic safety cast has reached a predetermined temperature, typically exhibiting a visual indicia when the predetermined temperature is reached; and allowing the orthopedic safety cast to set to a required hardness if the predetermined temperature has not been reached.

The step of applying the cast to a body member includes methods known and practiced to those in the art for applying casting bandages or tapes.

In some embodiments, the thermochromic materials are reversible and will change from an opaque color to a clear color. The desired colors and combinations of thermochromic and non-thermochromic materials can be determined by the orthopedic practitioner taking into consideration the particular body member to be cast and the condition of the underlying skin to be immobilized. The choice of predetermined temperatures and, therefore, the choice of thermochromic material(s) could easily be determined by one skilled in the art of casting tape/bandage manufacturing.

In some embodiments, the body member to be immobilized can first be covered with conventional cast padding or wrapped in a stockinette to protect the body part. Next, the curable casting material is cured in air, water or non-aqueous solution and then applied to the body member by wrapping the body member with the casting material with 1 to 20 layers, preferably 2 to 10 layers, of the casting material. The material is then molded and smoothed to conform the body member. The number of layers applied can vary depending on the degree of flexibility permitted, the particular body member to be immobilized and the intended function of the cast.

The step of monitoring the curing process of the casting material can typically involve visually monitoring the color development and color changes occurring on the perimeter or surface of the cast. The monitoring period required to ensure that the temperature of the cast has not reached an unsafe level can depend on several factors, including, by way of example, the number of layers of casting material applied, the temperature of the curing agent, and the type of curable matrix employed. Typically, the monitoring step can take from the initial placement of the cast to 30 minutes thereafter.

The safety cast of the present technology can have temperature sensing thermochromic materials that can alert the casting practitioner of cast temperatures that have medically been shown to cause burns. In this regard, monitoring the temperature change of the cast will enable the practitioner to determine the temperature of the cast in contact with the skin. Predetermined temperatures of the thermochromic materials are known and any such color change particularly for those thermochromic materials with color change temperatures at or above a known burning temperature can alert the casting practitioner that the cast should be removed or cooled. In some embodiments the predetermined temperature is from 37° C. to 48° C. If there is no visual indicia of a predetermined temperature that is correlated to a potentially hazardous temperature, the cast is allowed to harden completely. In some embodiments, the cast is allowed to harden if the cast does not reach 43° C. However, there can be other temperatures that are below 43° C. that can be hazardous for a particular patient or medical condition. In some embodiments, the predetermined temperature of the thermochromic material, (i.e. the color change temperature that results in a change of color from one color to another different color) can be selected based upon the needs of the patient and/or patient type. Such diagnosis of hazardous temperatures and the selection of appropriate thermochromic materials having visual indicia of such hazardous temperatures can be readily ascertained by the physician and the manufacturer of thermochromic materials.

Kits

The present technology also provides kits for the formation of an orthopedic cast, comprising a casting material of this technology and one or more components to facilitate the formation of a cast. For example, the kits may comprise a flexible substrate coated or impregnated with a curable casting matrix, a thermochromic material operable to exhibit an indicia (i.e., an indication) when the casting material reaches or exceeds a predetermined temperature; and instructions for forming a cast therefrom comprising information which correlates the indicia with the predetermined temperature, in a suitable package. The kits of the present disclosure can comprise a first thermochromic material operable to exhibit a first indicia when the casting material reaches or exceeds a first predetermined temperature, and a second thermochromic material operable to exhibit a second indicia when the casting material reaches or exceeds a second predetermined temperature, wherein the instructions for forming a cast therefrom that comprises information for correlating the first and second indicia with the first and second predetermined temperatures. When the cast material is a water-curable, air-drying formulation or a thermoplastic casting matrix, it is preferred for the casting material to be hermetically or vacuum sealed in a compartment of the kit.

The kit can further include gloves suitable for wearing during the cast molding process. Suitable gloves that can be used to handle the tacky material include gloves made from vinyl (such as polyvinyl chloride), latex, butyl rubber, or other such elastomeric materials.

In various embodiments, the kits additionally comprise a casting aid comprising a substrate, and a lubricating material coated on at least one surface of the substrate. During formation of a cast, the casting aid may be used to apply lubricant to the casting material or to the gloves of the casting practitioner, so as to aid in the formation of the cast. The casting aid can be packaged in the same compartment as the casting material in the kit, or in a different compartment which can be sealed or unsealed. In a preferred embodiment, the casting material comprises a roll of sheets, around the circumference of which the casting aid is wrapped.

The following non-limiting example illustrates the compositions and methods of the present technology.

EXAMPLE

A casting material according to this technology is made comprising a casting tape of fiberglass with approximately 12% polypropylene fiber, about 7.6 cm (3 inches) wide and 3.7 m (4 yards) long and 1 mm (4 mil) thick. The tape has approximately 25% stretch and a mesh size at approximately 40.3 holes/cm$^2$ (260 holes/in$^2$). A 230-meter (250-yard) roll of casting tape is partially fused by applying a narrow band of heat at approximately 315° C. (600° F.), at 3.7-meter (4-yard) intervals. The roll is then dried at approximately 110° C. (230° F.) for approximately 4 hours.

A curable Plaster of Paris matrix containing thermochromic and non-thermochromic dyes/pigments composition is made as having the following composition:

| Material | % (by weight) |
|---|---|
| Plaster of Paris[1] | 59.7 |
| Binder[2] | 1.5 |
| blue thermochromic water based slurry[3] | 2.2 |
| Red water based ink[4] | 0.8 |
| water | 35.8 |
| Total | 100.0 |

[1] Plaster of Paris, Synthetic Plus TM Plaster sold by DePuy Co., Warsaw, IN
[2] Binder is Vinnapas RE 5034 N sold by Wacker Chemical Corp., Adrian, MI
[3] Blue thermochromic water based slurry having a color change temperature of 43 sold by Color Change Corporation, Streamwood, IL
[4] Red water based ink (Pigmatex Red 2YF) sold by SunChemical, Cincinnati, OH For the above exemplary application the composition includes the following amounts of materials in the order presented, with mixing following after each subsequent material is added: Thus, the process of making the exemplary composition includes providing 1 gram of binder material, adding 9 grams of water, mixing, adding 0.5 gram of red water-based ink, mixing, adding 1.5 grams of blue thermochromic water-based slurry, mixing, adding 15 grams of water, mixing, adding 40 grams of plaster, and mixing.

The composition can be made by admixture of the components with the Plaster of Paris being mixed last. The roll of casting tape is removed from the drying oven and passed through the purple colored Plaster of Paris casting matrix. After passing through the matrix, the tape is squeezed through rollers to remove excess plaster, so that the plaster is impregnated at a level of about 42% by weight of the final impregnated tape. The tape is then cut where fused, to form individual strips of tape that are 3.7 m (4 yards) in length. An individual tape is then wound on a cylindrical core described in U.S. Pat. No. 5,984,884, Alvarez et al., issued Nov. 16, 1999 (incorporated by reference herein). A casting aid is then wrapped around the roll of impregnated casting sheet. The wrapped roll is sealed in a foil pouch under nitrogen, along with a desiccant pouch, to make a kit according to this technology. The sealed pouch is later opened and the orthopedic casting article is removed. Using latex gloves, the roll of casting material covered with the casting aid is placed in water and squeezed twice while underwater. The roll is then taken out of the water and squeezed to remove excess amounts of water. The casting material is visually inspected to determine whether the curing water has caused the casting material to become hazardous. If the casting material remains purple, then the casting material can be applied to the body member to be immobilized. The covered roll is used to wet both gloves being worn by rolling it between the palms and wiping both palms, transferring lubricating material from the casting aid to the gloves. The casting aid is then laid aside and the wrapping process begun.

The casting sheet is next unrolled while wrapping the sheet around the limb of a human subject to form a cast. After the casting material (from 1 to 10 layers) has been applied, the cast can be visually inspected to determine whether the cast temperature is hazardous to the patient. In an exemplary application, the plaster casting material changes from a purple color to a red color when the temperature of the cast has reached 43° C. At 43° C., the casting material changes to a red color, signaling that the temperature of the cast is too high, and that the casting material should not be placed on the patient, or if the casting material is already on the patient, action is taken to prevent the burning of the skin, such as removing the cast or cooling the cast.

The embodiments and the examples described herein are exemplary and not intended to be limiting in describing the full scope of compositions and methods of the present technology. Equivalent changes, modifications and variations of some embodiments, materials, compositions and methods can be made within the scope of the present technology, with substantially similar results.

What is claimed is:

1. An orthopedic casting material comprising:
   (a) a curable casting matrix comprising Plaster of Paris,
   (b) a flexible substrate coated or impregnated with the curable casting matrix and;
   (c) a thermochromic material capable of producing a visible indication in the casting material when the casting material reaches or exceeds a predetermined temperature of from about 20° C. to about 60° C., at which the thermochromic material undergoes a change in its color state.

2. The orthopedic casting material according to claim 1 wherein the flexible substrate comprises fibers selected from the group consisting of acrylic fibers, fiberglass, polyester fibers, polypropylene fibers, polyaramide fibers, polyamide fibers, carbon fibers, glass fibers, polyethylene fibers, polyacrylonitrile copolymer fibers, cotton fibers, wool fibers, flax fibers, rayon fibers, and mixtures thereof.

3. The orthopedic casting material according to claim 1, wherein the flexible substrate comprises fiberglass.

4. The orthopedic casting material according to claim 1 further comprising a non-thermochromic dye or pigment, or mixture thereof.

5. The orthopedic casting material according to claim 1, wherein the thermochromic material is selected from the group consisting of reversible or non-reversible thermochromic dyes, thermochromic pigments, thermochromic liquid crystals, and mixtures thereof.

6. The orthopedic casting material according to claim 5, wherein the thermochromic material is operative to change from one color to another color, from a color to colorless, or from colorless to a color, at the predetermined temperature.

7. The orthopedic casting material according to claim 5, wherein the thermochromic material changes color reversibly.

8. The orthopedic casting material according to claim 5, wherein the thermochromic material changes color irreversibly.

9. The orthopedic casting material according to claim 1, wherein the predetermined temperature is from about 40° C. to about 48° C.

10. The orthopedic casting material according to claim 1, wherein the thermochromic material is provided dispersed in a binder medium.

11. The orthopedic casting material according to claim 1, wherein the casting material comprises microcapsules containing the thermochromic material.

12. The orthopedic casting material according to claim 11, wherein the microcapsules contain from about 0.01 to about 50% by weight of the thermochromic material.

13. The orthopedic casting material according to claim 11, wherein the microcapsules have a particle size of from about 1 to about 75 µm.

14. The orthopedic casting material according to claim 1, wherein the flexible substrate comprises the thermochromic material.

15. The orthopedic casting material according to claim 1, wherein the curable casting matrix further comprises a binder and a red non-thermochromic dye or pigment, the casting matrix containing the thermochromic material, and the thermochromic material comprises a blue thermochromic dye or pigment capable of exhibiting a color change from blue to colorless at about 43° C. to 48° C.

16. The orthopedic casting material according to claim 1, wherein said thermochromic material comprises a first thermochromic material capable of producing a first visible indication in the casting material when the casting material reaches or exceeds a first predetermined temperature at which the first thermochromic material undergoes a change in its color state, and a second thermochromic material capable of producing a second visible indication in the casting material when the casting material reaches or exceeds a second predetermined temperature at which the second thermochromic material undergoes a change in its color state.

17. An orthopedic casting material comprising:
(a) a curable casting matrix comprising Plaster of Paris,
(b) a flexible substrate coated or impregnated with the curable casting matrix, and
(c) a thermochromic material capable of producing a visual indication in the casting material when the casting material reaches or exceeds a predetermined temperature at which the thermochromic material undergoes a reversible change in its color state.

18. The orthopedic casting material according to claim 17, wherein the thermochromic material is selected from the group consisting of reversible thermochromic dyes, thermochromic pigments, thermochromic liquid crystals, and mixtures thereof.

19. The orthopedic casting material according to claim 18, wherein the thermochromic material is operative to change from one color to another color, from a color to colorless, or from colorless to a color, at the predetermined temperature.

20. The orthopedic casting material according to claim 17, wherein the predetermined temperature is from about 20° C. to about 60° C.

21. The orthopedic casting material according to claim 20, wherein the predetermined temperature is from about 40° C. to about 48° C.

22. The orthopedic casting material according to claim 17, wherein the flexible substrate comprises the thermochromic material.

23. The orthopedic casting material according to claim 17, wherein the curable casting matrix further comprises a binder and a red non-thermochromic dye or pigment, the casting matrix containing the thermochromic material, and the thermochromic material comprises a blue thermochromic dye or pigment capable of exhibiting a color change from blue to colorless at about 43° C. to 48° C.

24. The orthopedic casting material according to claim 17, wherein said thermochromic material comprises a first thermochromic material capable of producing a first visible indication in the casting material when the casting material reaches or exceeds a first predetermined temperature at which the first thermochromic material undergoes a change in its color state, and a second thermochromic material capable of producing a second visible indication in the casting material when the casting material reaches or exceeds a second predetermined temperature at which the second thermochromic material undergoes a change in its color state.

* * * * *